United States Patent [19]
Cooper

[11] 4,001,938
[45] Jan. 11, 1977

[54] DENTAL RESTORATION JIG
[76] Inventor: Abraham J. Cooper, 348 Country Club Lane, Pomona, N.Y. 10970
[22] Filed: Dec. 11, 1974
[21] Appl. No.: 531,473

Related U.S. Application Data
[62] Division of Ser. No. 379,856, July 16, 1973, Pat. No. 3,871,804.
[52] U.S. Cl. .................................................. 32/11
[51] Int. Cl.² ......................................... A61C 13/00
[58] Field of Search ............................. 32/11, 40 R

[56] References Cited
UNITED STATES PATENTS

| | | | |
|---|---|---|---|
| 3,553,839 | 1/1971 | Gores | 32/11 |
| 3,798,772 | 3/1974 | Eberhard | 32/11 |
| 3,931,677 | 1/1976 | Tinder | 32/11 |
| 3,932,939 | 1/1976 | Weissman | 32/11 |

Primary Examiner—Louis G. Mancene
Assistant Examiner—Jack Q. Lever
Attorney, Agent, or Firm—Albert F. Kronman

[57] ABSTRACT

A dental restoration fabricating device in which dowels are employed to locate and register teeth and teeth dies. The dowels are held in their original positions by plastic holders arranged on an adjustable fence surrounding a base which, in turn, supports an impression of the patient's mouth. An alternate form includes an alignment pin for more accurate location of the tooth dies.

2 Claims, 10 Drawing Figures

DENTAL RESTORATION JIG

BACKGROUND OF THE INVENTION

This application is a division of an application filed July 16, 1973 entitled Dental Restoration Jig, Abraham Cooper, inventor, Ser. No. 379,856, now U.S. Pat. No. 3,871,804.

During the manufacture of certain kinds of dental restorations, an impression of the patent's teeth and gums is made in wax or other suitable material. Then, after spreading a thin film of grease or oil on the impression, a quantity of casting material is poured into the impression to produce a simulation of the patent's teeth and gums knows as a "model" or "mold". Dowels or pins are then embedded in the model for each tooth and the casting material poured around them. Thereafter individual teeth in the form of dies and their supporting dowels are carefully cut away and removed from the casting. The individual tooth castings or dies serve as supports around which the artificial added teeth, caps, or crowns are built. In the course of completing the restoration it is necessary to remove the dies and dowels many times from the model and return them in the same orientation.

The above described procedure has many idsadvantages. When the dies are removed from the model, considerable time and careful work is required to prevent destruction of the model. When the dies are returned to the model, it is difficult to retain their proper alignment. Repeated insertion and removal of the dowels enlarges the holes in the model into which they fit, further contributing to the poor alignment of the teeth dies and causing the dies to fall out as they are being worked on.

The present invention provides a reproducible arrangement whereby dental restorations can be manufactured in less time and at a reduction in cost.

A feature of the invention is the use of a dowel and an alignment pin for removably and accurately holding a tooth die within a mold or model.

Another feature of the invention is the use of an adjustable rack which facilitates the pouring of the model forming material and the placement of tooth location members therein.

A further feature of the invention is the use of an adjustable rack having several positions whereby teeth models of varying sizes can be accommodated.

SUMMARY

The invention comprises a cylindrical base including a plurality of vertical pins secured to the base in spaced position. The base is formed with a central recess. A cup is provided for placement into the recess in the base for supporting an impression of a patient's teeth. The cup includes two wings, each formed with a recess for accurate placement on two of the vertical pins. A plurality of tables in provided, each formed with at least two hollow vertical tubes, for placement over selected pins on the base. The tubes also includes horizontal arcuate support bars, for supporting a plurality of dowel holders. The tables and their attached dowels may be readily removed or secured to the base during casting operations. The dowel holders are secured to the top surface of the support bars by putty or caulking material.

Additional details of the invention will be disclosed in the following description, taken in connection with the accompanying drawings.

DESCRIPTION OF THE PREFERRED EMBODIMENTS

Figure 1:
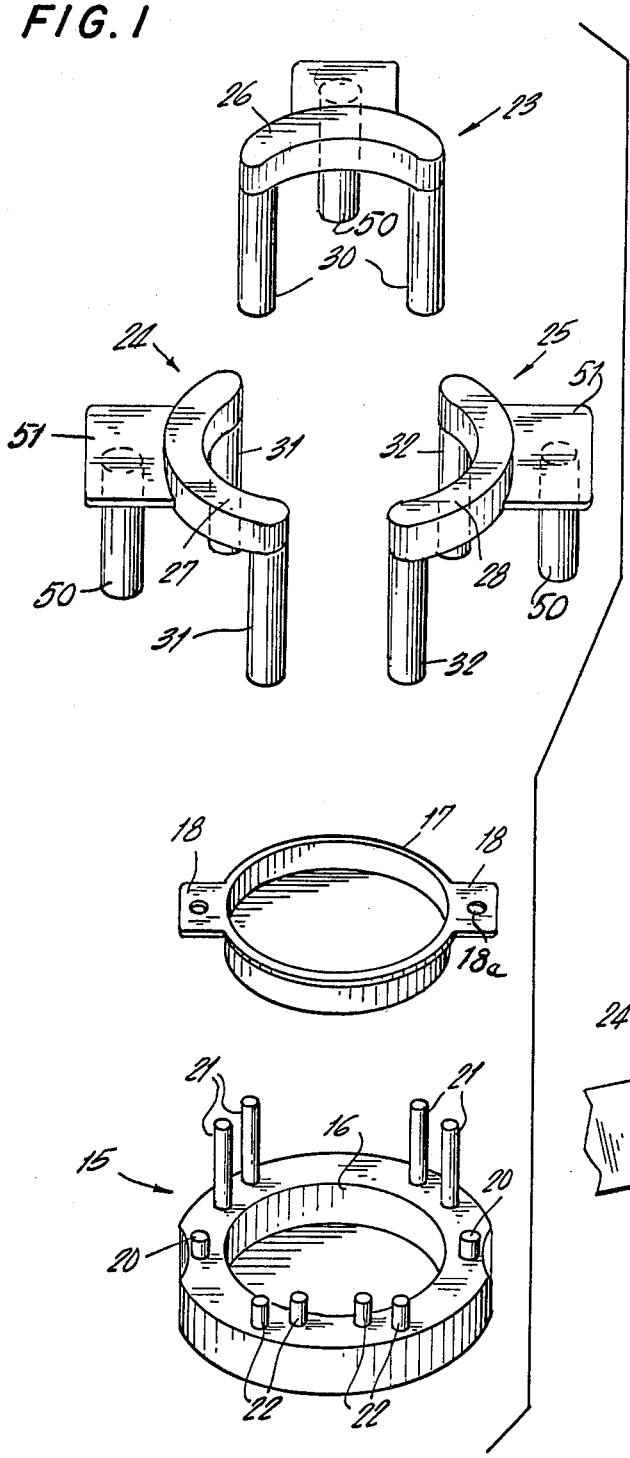
FIG. 1 is an exploded perspective view of one complete embodiment of the present invention.

Referring now to FIGS. 1 through 5, the dental restoration jig includes a base 15 having a generally cylindrical form including a central recess 16 for receiving a cup 17. The cup 17 is provided with wings 18, each formed with an indexing hole 18a. The base 15 is formed with two upstanding small pins 20 for engaging the holes 18a in wings 18 so that the cup 17 can be removed from the base and accurately replaced in its original position. The base 15 also includes a plurality of upstanding long pins 21 and shorter pins 22 for positioning other parts of the jig as hereinafter more fully set forth.

Figure 3:
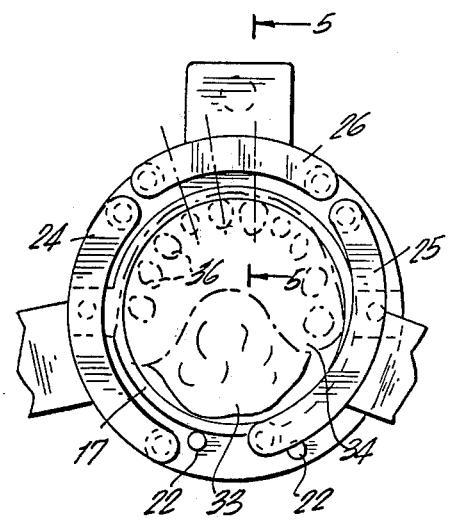
FIG. 3 is a plan view of the base, the cup, and three racks, in their operating position.

Three tables 23, 24 and 25 are shown in FIG. 1, each of the tables having an arcuate support portion 26, 27 and 28 for positioning dowel holders as will be explained later. The arcuate support portions are each formed integral with three downwardly extending hollow tubes 30, 31 and 32 which are designed to fit over pins 21 and 22 on the base 15. As shown in FIG. 3, two of the tubes 30 engage two pins 21; two of the tubes 31 engage one pin 21 and one pin 22; and two of the tubes 32 are placed over two other pins 21, 22.

Figure 2:
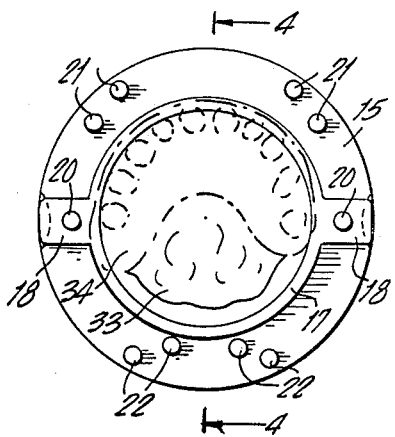
FIG. 2 is a plan view of the base with a cup in position thereon.
Figure 4:
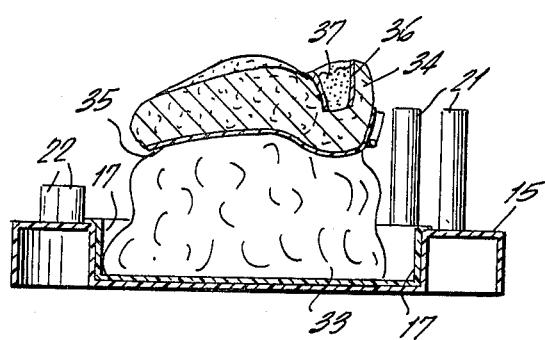
FIG. 4 is a cross sectional view of the components shown in FIG. 2 and is taken along line 4—4 of that figure.

FIGS. 2, 3 and 4 show the cup 17, filled with a mass of putty 33 which supports an impression 34 of a patient's mouth. The impression may be made in wax and held on a thin metal plate or "tray" 35. The impression 34 contains a number of depressions or recesses 36 made by the patient's teeth which are to be filled by casting material, such as cast stone, epoxy, or the like. In addition, and to facilitate further operations, a metal dowel 38 (FIG. 5) is secured within each tooth die. The lower end of the dowel 38 is knurled so that it will be securely held by the cast material. The upper end of the dowel during casting is held in vertical alignment by a dowel holder 40 enclosing a core 41 of elastic material such as neoprene, silicone rubber or the like. A small recess (not shown) is provided in the core to receive the end of the dowel. The small end of the dowel is pushed into the recess and is held there until the casting material 37 is hard.

Figure 5:
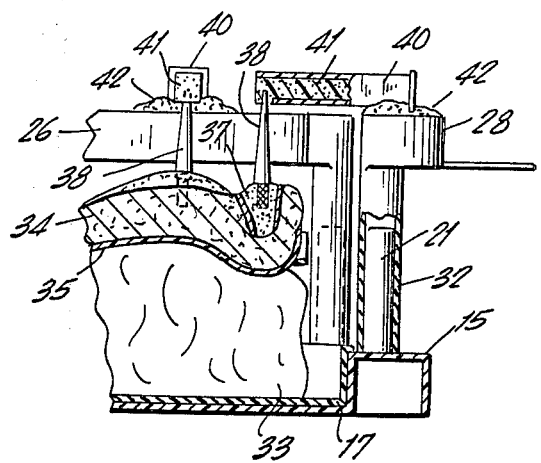
FIG. 5 is a partial cross sectional view of the components shown in FIG. 3 and is taken along line 5—5 of that figure. Dowels and dowel holders have been added to this view.

As indicated in FIG. 5 the ends of the dowel holders 40 are secured to the tables 28 by portions of putty or wax 42. The putty or wax portions are temporary fastenings and are maintained in place only long enough to permit the casting material 37 to harden around the dowels.

The operation of this jig is as follows: The dentist first makes an impression of the patient's teeth and gums in wax or similar material carried upon a supporting plate 35. Then the plate 35 is placed on a portion of wax or putty 33 held in the cup 17. If desired, the impression may be plated with silver or some similar metal to increase its wearing qualities. The tables 28 are now placed in position around the impression. Considerable leeway is available to the dentist since the spacing of the pins 21, 22 and the three tubes on each rack permit the adjustment of a table pattern for any type and size of restoration, either a full denture or a small bridge. FIG. 3 shows the right-hand rack 25 positioned a little closer than the left-hand rack 24. Dowel holders 40 and dowels 38 are then adjusted and secured to the tables with the required vertical orientation and location of each dowel to provide the necessary positioning of the dowels in the casting materials. At this stage of operations, the tables may be slipped off the pins for easy casting operations. A third tube 50 on each of the tables permits them to be placed on any convenient surface and a tab 51 facilitates handling.

The dentist or technician next pours a casting compound 37 into the recesses left by the patient's teeth and the tables and their dowels 37 (see FIG. 5) are lowered into the compound while it is still soft. The dowel 38 is attached to the core 41 of the holder 40 as shown in the figure. All the recesses are filled in this manner. After the castings have become hard, a coating of thick oil or grease is applied to the impression and some additional casting material added, this time over the entire impression to make a model or mold of the patient's teeth, gums, and part of his mouth. The ends of the cores 41 extend outwardly of the casting material. This step is well-known and need not be described here in detail. The final casting material covers the length of the dowels and overlies the cores. It should be noted that this final model is different from the usual model because the top surface of the individual teeth dies 37 are separated from the final casting material by a thin film of oil.

The impression 34 and its tray 35 are now removed from the second or model casting and what remains is a positive impression or model of the patient's teeth and gums. Each tooth die can now be removed by pulling the soft core out of the casting material and cutting the material between adjacent teeth. A small instrument can then be applied, lifting it and the die out of the casting. Separation is made between the tooth die and the rest of the casting at the surface where the first coating of oil was applied. The tooth and its dowel can be replaced again for fittings of bridge crowns, caps or any other type of restoration.

Figure 6:
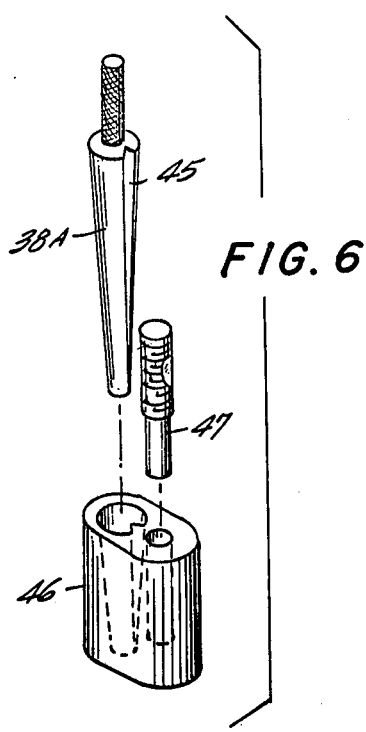
FIG. 6 is an isometric exploded view of a dowel and an alignment pin together with an alignment sleeve. These components comprise an alternate form of the invention.
Figure 7:
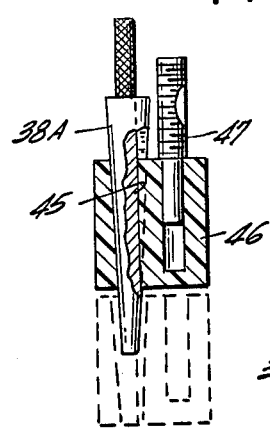
FIG. 7 is a cross sectional view of the components shown in FIG. 6 but in their assembled positions.
Figure 10:
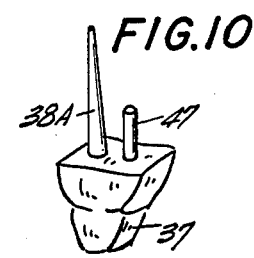
FIG. 10 is a perspective view of a tooth die taken from a model along with its dowel and alignment pin.
Figure 8:
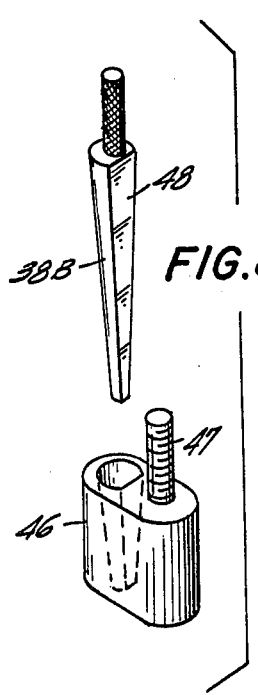
FIG. 8 is an isometric view of the components shown in FIG. 6 but with a dowel having a flat face and the pin in its operational position within the alignment sleeve.

FIGS. 6 through 10 show a somewhat modified type of dowel arrangement. In this alternate type the dowel 38a, shown in FIG. 6, is formed with a V-shaped channel 45 and it is fitted into an alignment sleeve 46 together with an alignment pin 47. The dowell 39a is made of metal or any other rigid material as is the pin 47, preferably stainless steel or brass. The alignment sleeve 46 can be made of plastic. FIG. 8 shows a similar arrangement with the dowel 38b formed with a flat portion 48. Any non-circular tapered cross sectional shape will serve for the dowel. The alignment pin is preferably shorter than the dowel and may be threaded into the sleeve as shown. FIG. 7 is a partial cross sectional view showing the dowel 38a and the alignment pin 47 assembled in the sleeve 46 ready for application to the tooth casting.

Figure 9:
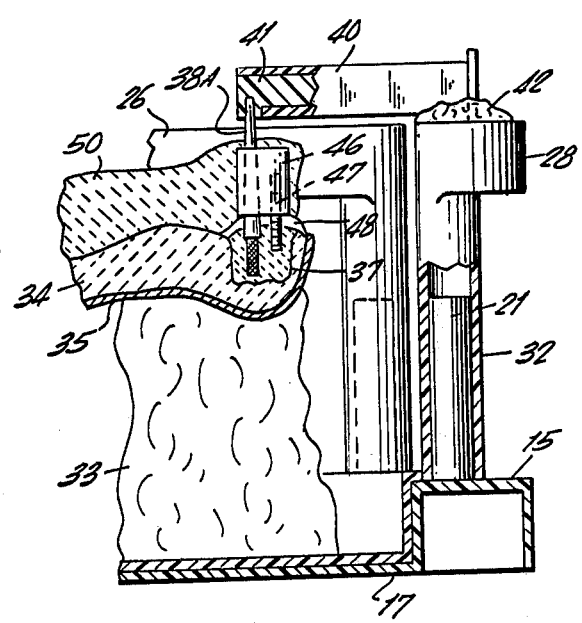
FIG. 9 is a partial cross sectional view similar to FIG. 5 but showing the alternate dowel alignment means.

FIG. 9 can be used to illustrate the operation of the alternate form. The impression of the patient's teeth and gums is made in the usual manner. The result is an impression in wax 34 on a tray 35 with recesses conforming to the teeth. The tray 35 is put on a wad of putty 33 in cup 17 inside the jig 15. Next, a casting compound 37 is poured into the teeth recesses and the lower ends of a dowel 38a and an alignment pin 47 are pushed into the soft compound. The alignment sleeve 46 is maintained in its position during the entire operation. A coating of heavy oil or grease is applied to the wax 34 as soon as the compound 37 is hard and an additional layer of wax 48 may be applied to the top of the tooth die 37 to fill the space between the top of the die 37 and the bottom surface of the alignment sleeve 46. A permanent casting material 50 is now added to the top of the impression and also surrounding the alignment sleeve 46. As soon as the casting material 50 is hard, the impression of wax 34 and the tray 35 can be removed and there remains a model of the patient's mouth with each tooth die secured to a dowel and an alignment pin.

Each tooth die can now be removed independently of the other dies by cutting the cast material between adjacent teeth. A small flat instrument may be used to lift the dowel and the die out of the casting. After removal, the dies can be accurately replaced to their former position by means of the alignment sleeve and pin. The alignment pin prevents any swivel rotation of the cast tooth.

Having thus fully described the invention, what is claimed as new and desired to be secured by Letters Patent is:

1. A dowel assembly for casting models of individual tooth impression into dental impression tooth recesses comprising an alignment sleeve having spaced first and second bores therein, a rigid dowel pin received within a first bore and extending therethrough, and adapted to extend into an individual tooth recess, and a rigid alignment pin received within the second bore and extending therefrom and adapted to extend into the said individual tooth recess.

2. A dowel assembly according to claim 1 in which the dowel pin is tapered for at least a portion of its length and the said tapered portion is on non-circular cross section.

* * * * *